US008702617B2

(12) United States Patent
Peters

(10) Patent No.: US 8,702,617 B2
(45) Date of Patent: Apr. 22, 2014

(54) SIMULTANEOUS AMBULATORY PULSE OXIMETRY AND PH MONITORING FOR THE DIAGNOSIS OF GERD-RELATED RESPIRATORY DISEASE

(75) Inventor: Jeffery H. Peters, Pittsford, NY (US)

(73) Assignee: University of Rochester, Rochester, NY (US)

(*) Notice: Subject to any disclaimer, the term of this patent is extended or adjusted under 35 U.S.C. 154(b) by 547 days.

(21) Appl. No.: 12/768,182

(22) Filed: Apr. 27, 2010

(65) Prior Publication Data

US 2010/0280337 A1    Nov. 4, 2010

Related U.S. Application Data

(60) Provisional application No. 61/173,774, filed on Apr. 29, 2009.

(51) Int. Cl.
| | | |
|---|---|---|
| *A61B 5/14551* | (2006.01) | |
| *A61B 5/0205* | (2006.01) | |
| *A61B 5/021* | (2006.01) | |
| *A61B 5/085* | (2006.01) | |

(52) U.S. Cl.
USPC ........... 600/529; 600/301; 600/309; 600/323; 600/350; 600/361; 600/484; 600/485; 600/533; 600/547

(58) Field of Classification Search
CPC .......................... A61B 5/14539; A61B 5/4211
USPC ......... 600/301, 309, 323, 350, 361, 484, 485, 600/529, 532, 533, 547
See application file for complete search history.

(56) References Cited

U.S. PATENT DOCUMENTS

| | | | | |
|---|---|---|---|---|
| 5,357,954 A | * | 10/1994 | Shigezawa et al. | 600/339 |
| 5,810,741 A | * | 9/1998 | Essen-Moller | 600/529 |
| 7,236,820 B2 | * | 6/2007 | Mabary et al. | 600/547 |
| 2003/0028088 A1 | * | 2/2003 | Castell et al. | 600/350 |
| 2005/0065450 A1 | * | 3/2005 | Stuebe et al. | 600/547 |
| 2006/0116564 A1 | * | 6/2006 | Mintchev et al. | 600/350 |
| 2006/0270940 A1 | * | 11/2006 | Tsukashima et al. | 600/529 |
| 2007/0068811 A1 | * | 3/2007 | Tsukashima et al. | 204/433 |
| 2007/0225576 A1 | * | 9/2007 | Brown et al. | 600/301 |
| 2008/0234599 A1 | * | 9/2008 | Chiao et al. | 600/547 |
| 2009/0026078 A1 | * | 1/2009 | Wolf et al. | 204/433 |
| 2009/0326390 A1 | * | 12/2009 | Belalcazar et al. | 600/486 |

OTHER PUBLICATIONS

Castell et al, Non-acid Gastroesophageal Reflux: Documenting its Relationship to Symptoms Using Multichannel Intraluminal Impedance (MII), 2005, Transactions of the American Clinical and Climatological Association, vol. 116, pp. 321-334.*

Salvador et al, Association of Gastroesophageal Reflux and O 2 Desaturation: A Novel Study of Simultaneous 24-h MII-pH and Continuous Pulse Oximetry, Feb. 2009, The Society for Surgery of the Alimentary Tract, pp. 854-861.*

* cited by examiner

*Primary Examiner* — Jacqueline Cheng
*Assistant Examiner* — Puya Agahi
(74) *Attorney, Agent, or Firm* — Blank Rome LLP

(57) ABSTRACT

Respiratory diseases related to gastroesophageal reflux disease in a patient are diagnosed by detecting esophageal or pharyngeal impedance and pH in the patient, detecting oxygen saturation in the patient, and diagnosing the respiratory diseases from the esophageal or pharyngeal impedance, the pH, and the oxygen saturation.

14 Claims, 15 Drawing Sheets

SIMULTANEOUS AMBULATORY PULSE OXIMETRY AND PH MONITORING FOR THE DIAGNOSIS OF GERD-RELATED RESPIRATORY DISEASE

REFERENCE TO RELATED APPLICATION

The present application claims the benefit of U.S. Provisional Application No. 61/173,774, filed Apr. 29, 2009, whose disclosure is hereby incorporated by reference in its entirety into the present disclosure.

FIELD OF THE INVENTION

The present invention is directed to the diagnosis of respiratory diseases related to GERD (gastroesophageal reflux disease) and more particularly to such diagnosis which uses reflux events and $O_2$ desaturation.

DESCRIPTION OF RELATED ART

Respiratory symptoms have long been recognized to be associated with gastroesophageal reflux disease (GERD). Indeed, Sir William Osler noted over 100 years ago that asthmatics "learn to take their large daily meal at noon in order to avoid nighttime asthma which occurred if they ate a full supper." It is known that GERD is more often observed in asthmatic patients than in the general population. Cough, wheezing, hoarseness, or recurrent pneumonia are present in as many as 50% of patients with GERD, and respiratory complaints are the primary or sole symptoms in 20%. Experimental data show that gastroesophageal reflux stimulates physiologic responses in the upper respiratory tract, and direct contact with refluxed material may result in significant pathologic injury including end-stage pulmonary fibrosis. Two pathophysiologic mechanisms are known to occur: microaspiration of gastric contents and vagal reflex responses. In the first mechanism, the reflux of gastric contents may directly overflow into the upper and lower airways, causing symptoms and tissue damage. With the second mechanism, reflux of gastric contents can stimulate vagus nerve terminals, provoking a reflex cough or bronchoconstriction. Pathologic changes in the respiratory tract suggesting an association with GERD have been detected in up to 80% of patients with asthma. The association between GERD and respiratory symptoms is further supported by the improvement or resolution of symptoms after surgical or medical treatment of reflux.

GERD is a known cause of asthma, cough, recurrent pneumonia, lung abscess, and pulmonary fibrosis leading to end-stage pulmonary failure. In fact, the term "gastroesophageal reflux disease" is an oversimplification in that reflux can occur at multiple levels within the upper aerodigestive tract, not merely across the gastroesophageal junction. Of relevance to the development of pulmonary symptoms is the potential for esophagopharyngeal reflux and pharyngotracheal reflux, potentially exposing the airways and pulmonary parenchyma to duodenal and gastric contents. The term "laryngopharyngeal reflux" has also arisen to denote reflux into the upper airway.

A number of modalities traditionally have been utilized to objectify the presence of GERD. The gold standard test is ambulatory esophageal pH monitoring, though the presence of GERD can also be deduced by the presence of significant erosive esophagitis or Barrett's esophagus on endoscopic assessment or the finding of a hiatal hernia with reflux on barium esophagography. When the patient complains of typical reflux symptoms such as heartburn or regurgitation, such objectification of GERD has proven highly reliable in determining that GERD is causative. When the patient's primary symptoms are respiratory in nature, such a cause-and-effect relationship to GERD has proven much more elusive. While testing can objectify the presence of GERD, whether GERD is actually contributing to the respiratory complaints may be less than certain. GERD and conditions such as asthma or cough are common and can coexist without being related. In addition, symptoms alone are unreliable in determining such an association, and there is no pathologic mucosal abnormality, as detected on histologic assessment of biopsies from the esophagus, larynx, or airways, that is pathognomonic for the presence of GERD. Occult GERD can occur in the absence of typical symptoms, and reflux of even small amounts of gastric juice occurring at a remote point in time can induce a lingering cough or precipitate a prolonged asthma exacerbation. Repetitive microaspiration episodes can lead to chronic pulmonary parenchymal damage and the insidious onset of "idiopathic" pulmonary fibrosis. The fact that GERD can be a contributor to end-stage lung disease and the development of posttransplant obliterative bronchiolitis or infection has been demonstrated in the lung transplant literature.

Due to the unreliability of commonly utilized testing methods in proving that GERD is etiologic to respiratory symptoms, a common diagnostic paradigm is a therapeutic trial of intensive acid suppressive therapy to assess clinical response. While such a strategy may prove effective in a subset of cases, inherent deficiencies exist in such a protocol. Cough or asthma may improve spontaneously or due to other medical therapies and be unrelated to GERD. On the other hand, nonacid reflux may persist despite intensive acid suppression, leading to persistent complaints even when GERD is causative. Combined MII-pH monitoring has arisen as a tool to detect nonacid reflux. A symptom index can be calculated while on medical therapy and has been shown to predict a response to subsequent antireflux surgery.

Objectively identifying this association is a major clinical challenge. There is currently no diagnostic method which reliably confirms that respiratory symptoms are secondary to the presence of gastroesophageal reflux. As a result, treatment outcomes are less predictable than with typical esophageal symptoms.

Current diagnostic techniques have not shown adequate sensitivity or specificity for detection of gastroesophageal reflux in patients presenting with respiratory complaints. Thus, establishment of a causal relationship between refluxed materials into the esophagus and consequent respiratory symptoms still remains a challenge.

SUMMARY OF THE INVENTION

It is therefore an object of the invention to provide such a diagnostic technique.

It has been demonstrated that oxygen desaturation coincides with episodes of increased esophageal acidity, as detected by pH monitoring, in 40% of patients with COPD (chronic obstructive pulmonary disease). This fact, combined with studies showing that esophageal acidification causes an increase in airway resistance, led us to hypothesize that oxygen desaturation may occur following episodes of gastroesophageal reflux and that this association may be useful in distinguishing patients with reflux-related respiratory symptoms from those whom reflux may not be causative. The advent of continuous ambulatory $O_2$ saturation monitoring made it possible to simultaneously assess the association of gastroesophageal reflux with $O_2$ saturation in patients with and without primary respiratory symptoms using combined simultaneous ambulatory monitoring systems.

An important aspect of the present invention is the combination of esophageal (or pharyngeal) impedance and pH measurement with oxygen saturation, doing so simultaneously in some embodiments, and the development of interpretation algorithms that have clinical validity. The construction of a device containing both types of sensors and allowing simultaneous second by second matched data collection are also within the scope of the invention.

Due to the inherent inaccuracies of all of the commonly utilized testing methodologies for GERD in the setting of primary respiratory complaints, the potential for a simple, noninvasive, inexpensive, easily available, and readily applied test holds significant appeal. Ambulatory oxygen saturation monitoring with pulse oximetry is such a diagnostic modality. Application and utilization of the device requires no special training and is readily tolerated by patients with excellent compliance and minimal discomfort.

We sought to improve our understanding of the causal relationship between refluxed materials into the esophagus and consequent respiratory symptoms using combined 24-hour impedance-pH and pulse-oximetry monitoring in both normal subjects to establish relative comparative thresholds, as well as in symptomatic patients presenting with both primary respiratory, as well as primary gastrointestinal symptoms.

In summary, combined ambulatory MII-pH and pulse oximetry monitoring revealed a high prevalence of oxygen desaturations in temporal proximity to reflux events, particularly in patients complaining primarily of respiratory symptoms. This novel observation adds to our understanding of the pathogenesis of GERD-related respiratory symptoms.

BRIEF DESCRIPTION OF THE DRAWINGS

A preferred embodiment will be set forth in detail with reference to the drawings, in which.

DETAILED DESCRIPTION OF THE PREFERRED EMBODIMENT

First, a study to validate the concept will be disclosed. Then, a device for use will be taught.

The study population consisted of 30 patients with symptoms of GERD undergoing foregut diagnostic evaluation between January, 2007 and April, 2008. There were 20 women and ten men with a mean age of 48 years, ranging between 18 and 73 years. Patients having undergone previous upper gastrointestinal (GI) surgery or esophageal dilatation were excluded. All underwent simultaneously timed 24-hour multichannel intraluminal impedance (MII)-pH and continuous $O_2$ saturation monitoring via pulse oximetry as well as esophageal manometry, upper endoscopy, and video barium upper GI examination.

A structured questionnaire to assess foregut symptoms was administered prior to objective testing. The presence and severity of respiratory symptoms including cough, hoarseness, and wheezing, and/or esophageal symptoms including heartburn, regurgitation, or dysphagia were recorded at the initial visit. Based upon the most bothersome symptom reported, patients were classified into two groups: those with primary respiratory and those with primary esophageal symptoms.

Simultaneous ambulatory reflux testing using a transnasal MII/pH catheter (Sandhill Scientific, Denver, Colo., USA)

and pulse oximetry was performed on each subject. The MII/pH catheter consisted of six pairs of impedance electrodes and one or two pH sensors. Two catheters were utilized: (a) MII/pH catheter with pH sensor placed 5 cm above the proximal border of the lower esophageal sphincter (LES) and impedance sensors at 3, 5, 7, 9, 15, and 17 cm above the LES and (b) MII/pH catheter with pH sensors placed 5 and 20 cm above the proximal border of the LES and the impedance sensors 3, 5, 7, 9, 15, and 17 cm above the LES. After calibration, the MII/pH probe was passed transnasally and positioned based upon the location of the LES as determined by manometry. Data were acquired and analyzed using BioView analysis software (Sandhill Scientific, Denver, Colo., USA).

Figure 1:
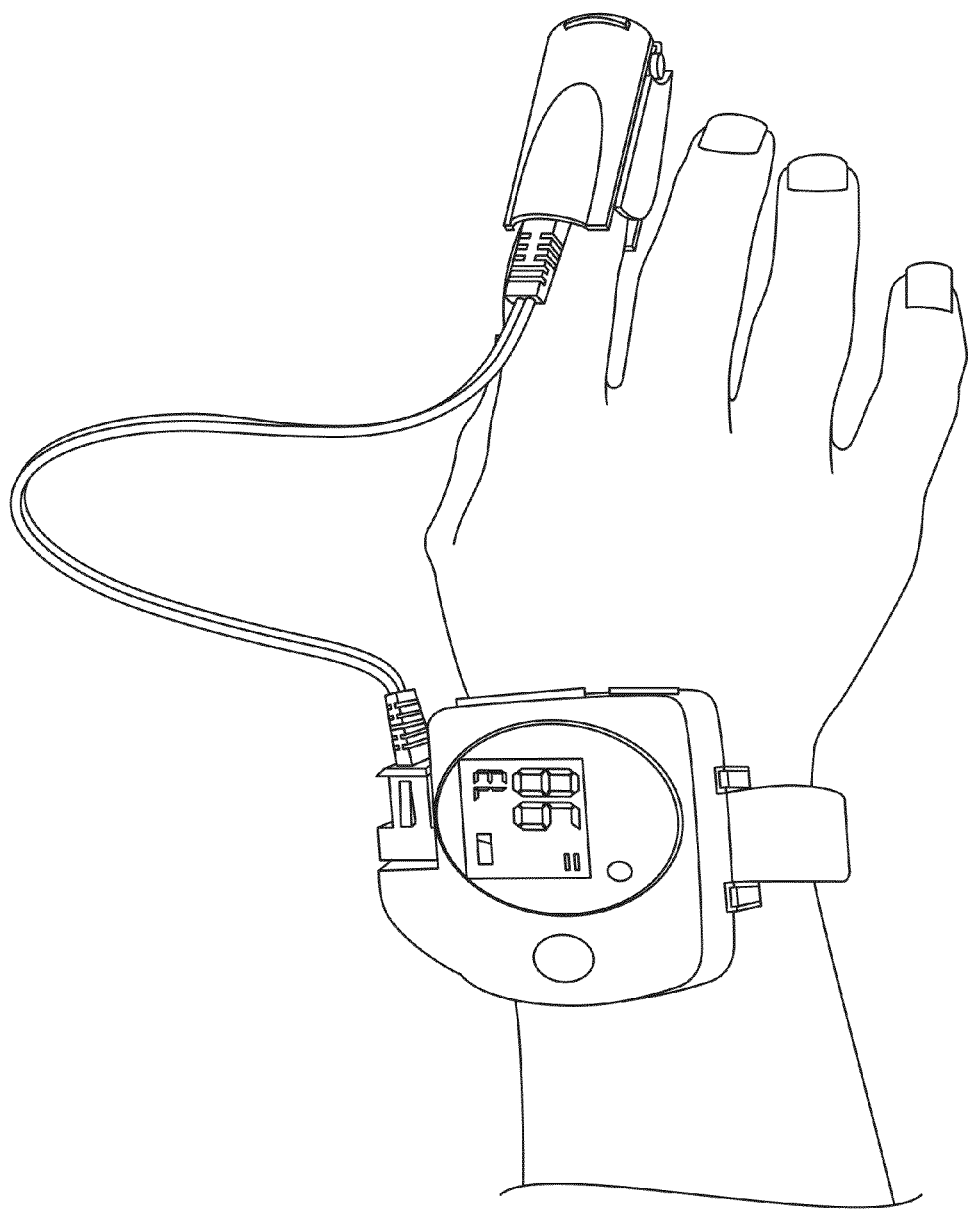
FIG. 1 shows an oximetry finger probe.

Oxygen saturation monitoring was performed using the Pulsox-300i (Konica Minolta Sensing, Inc.) and Finger Clip Probe SR-5C (Konica Minolta; FIG. 1). Pulsox-300i measures the oxygen saturation ($SpO_2$) in arterial blood and pulse rate at a frequency of once per second via the standard photometric noninvasive method as employed in everyday clinical practice. $SpO_2$ is defined by the following equation:

$$SpO_2 = \frac{C(HbO_2)}{C(HbO_2) + C(Hb)} \times 100(\%SbO_2)$$

where
$C(Hb)$=concentration of reduced hemoglobin, and
$C(HbO_2)$=concentration of oxyhemoglobin.

The instrument measures changes in the absorption of red and infrared light passing through tissues to determine the $SpO_2$ of the blood. Measurements range from 0% to 100% for $SpO_2$ and 30 to 230 bpm for pulse rate. Manufacturer's data reveal that the Pulsox-300i accuracy for $SpO_2$ is ±2% (70% to 100% range) and for pulse rate is ±2 bpm (30 to 100 bpm range) or ±2% of value (100 to 230 bpm range).

Data were acquired and analyzed using Profox Oximetry Software (Profox Associates, Inc., Escondido, Calif., USA). The timing of the pulse oximetry was synchronized with the MII-pH study at the onset of the study period. The time drift for the first ten patients was between 15 and 18 s. The Pulsox-300i was secured to the wrist and the probe placed on the index finger in all patients.

Proximal reflux was defined by the occurrence of pH<4 20 cm above the LES or reflux in the two proximal impedance sensors located 15 and 17 cm above the LES. Reflux events occurring outside the time of continuous oxygen saturation monitoring were not assessed in this study. An abnormal 24-h MII-pH study was defined as a DeMeester score >14.72 or the presence of more than 26 weakly acidic reflux episodes or one alkaline reflux episode (pH>7).

Figure 2:
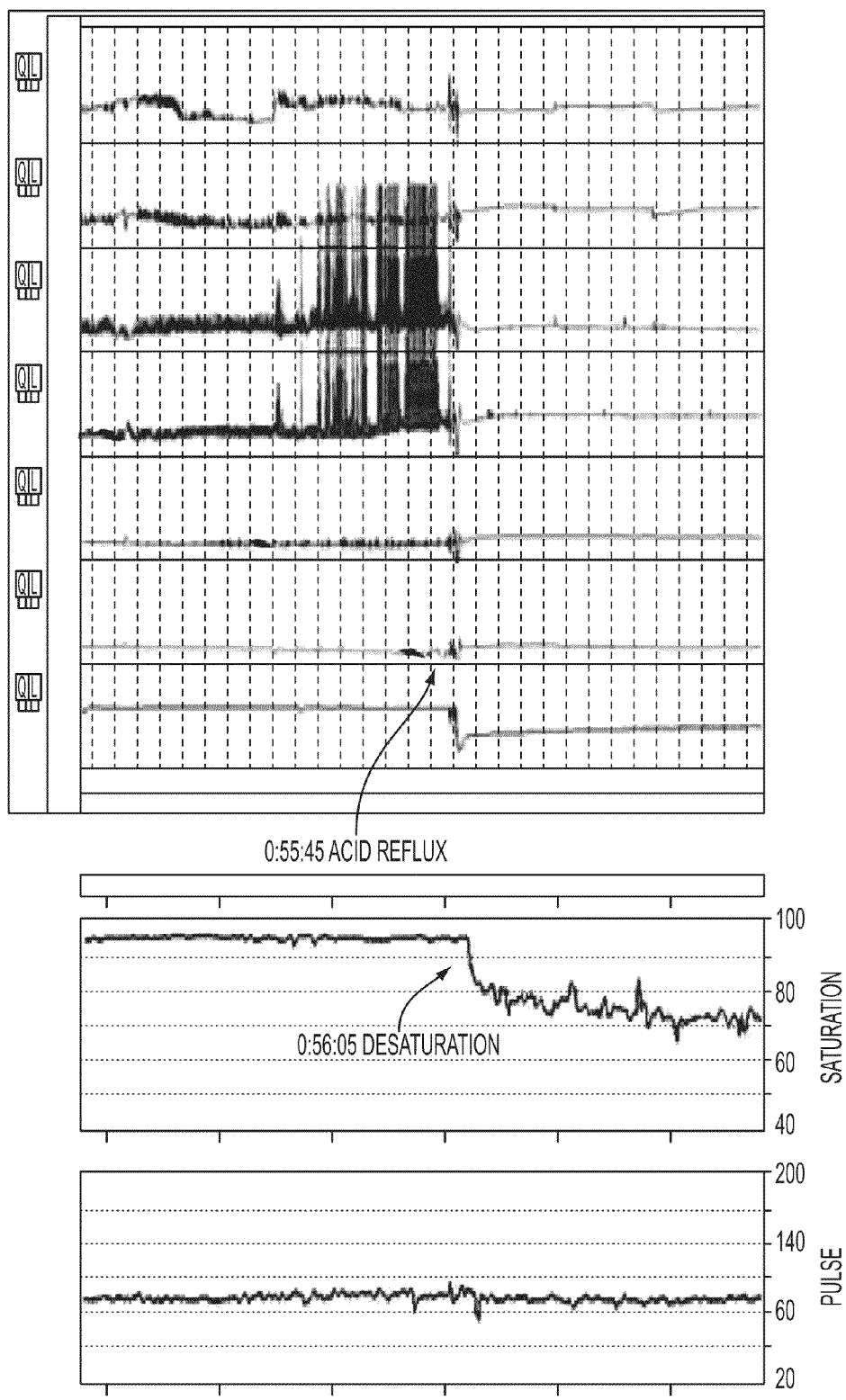
FIG. 2 shows the association between a reflux episode detected by the MII-pH study and oxygen desaturation detected by pulse oximetry.

Oxygen desaturation events were defined by one of two observations: (1) $SpO_2$<90% or (2) $SpO_2$ drop of 6% or greater. A reflux-desaturation association was considered present if $O_2$ desaturation occurred within 30 s prior to or 10 min after a reflux event (FIG. 2).

Comparisons between groups were performed using Student's t test. Descriptive data for each measured parameter were expressed as mean±standard error of the mean (SEM). A p value of less than 0.05 was considered significant.

Twenty patients had primary respiratory symptoms, including cough in 15 (75%), hoarseness in 12 (60%), and wheezing in five (25%). Respiratory symptoms were the sole symptoms in two patients (10%). Ten patients with primary esophageal symptoms, including heartburn in all, regurgitation in eight (80%), chest pain in five (50%), dysphagia in three (30%), and epigastric pain in one (10%) were used as a comparison group. Clinical features of the two groups are shown in Table 1.

TABLE 1

Objective Findings in the Two Patient Groups as Detected by Endoscopy, Barium Esophagography, Manometry, and pH/Impedance

| | Respiratory symptoms (n = 20) | Esophageal symptoms (n = 10) |
|---|---|---|
| Hiatal hernia | 15 (75%) | 9 (90%) |
| Erosive esophagitis | 6/16 (37.5%) | 5/9 (55.5%) |
| Barrett's esophagus | 1/16 (6.2%) | 2/9 |
| Defective lower esophageal sphincter | 12 (60%) | 8 (80%) |
| Ineffective motility | 6 (30%) | 1 (10%) |
| Positive distal esophageal acid exposure | 14 (70%) | 5 (50%) |

Figure 3A:
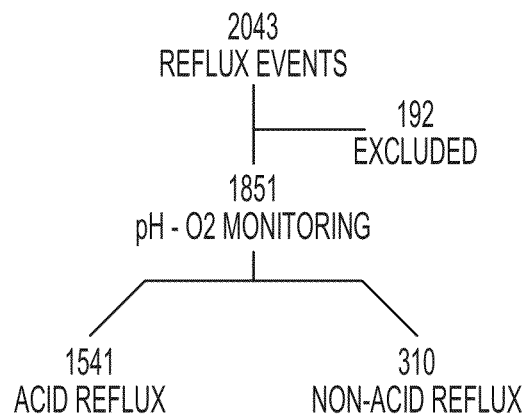
FIG. 3a shows the distribution of reflux into acid reflux events and nonacid reflux events.
Figure 3B:
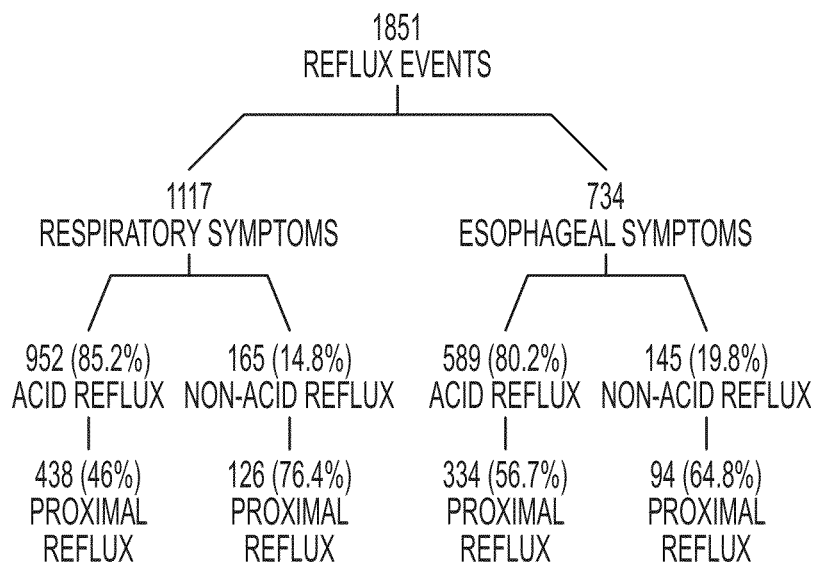
FIG. 3b shows the distribution of reflux events by patient group.
Figure 4:
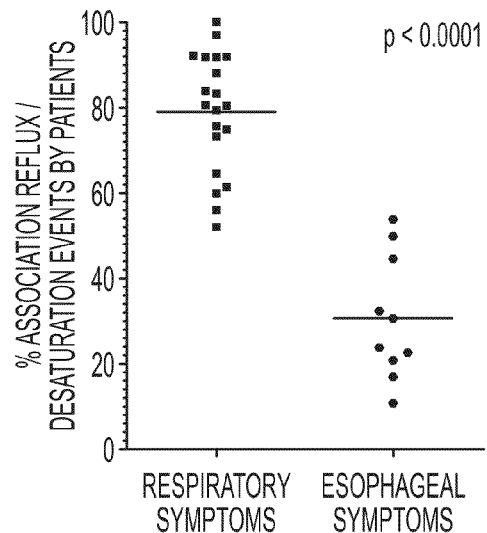
FIG. 4 is a scatter plot of the association between reflux episodes and desaturation events by patient group.

Abnormal esophageal acid exposure was present in 19 of the 30 patients (14 respiratory, five esophageal symptoms) and was at the upper limit of normal in two (both respiratory group). MII-pH study detected 2,043 reflux episodes of which 1,851 were correlated with continuous $O_2$ saturation monitoring (FIG. 3a). One hundred ninety-two reflux events were not included in the study because of technical problems with simultaneous $O_2$ saturation monitoring. The reflux was characterized as acid in 1,541 (average 51 events per patient) and nonacid in 310 (average ten events per patient; FIG. 3b). One thousand one hundred seventeen reflux events occurred in patients with primary respiratory symptoms and 734 in those with primary esophageal symptoms. Nearly 60% of the 1,851 reflux events were associated with $O_2$ desaturation. Overall, significantly more reflux events of any type were associated with $O_2$ desaturation in patients with respiratory symptoms (74.5%) than in patients with esophageal symptoms (30.4%, p<0.0001; FIG. 4).

Figure 5:
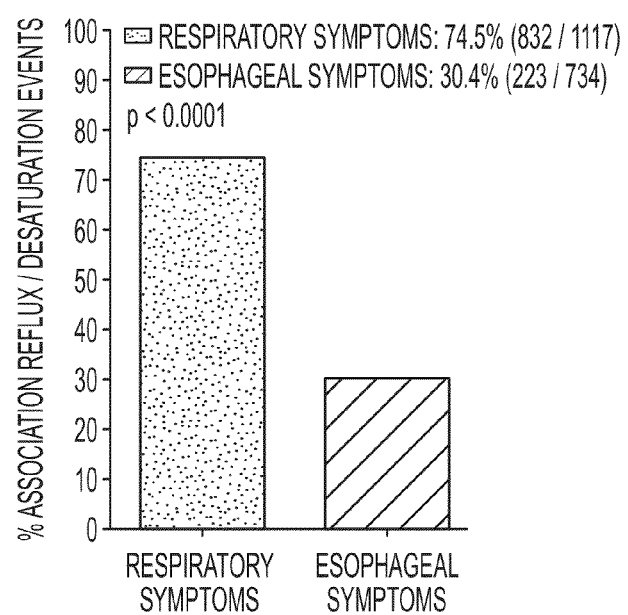
FIG. 5 is a bar chart of the association between reflux episodes and desaturation events.
Figure 6:
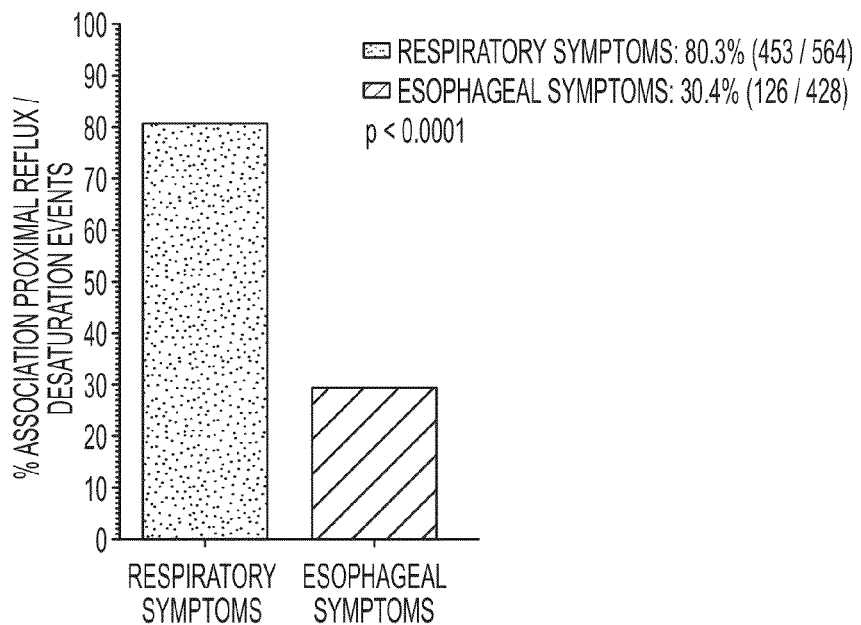
FIG. 6 is a bar chart of the association between proximal reflux episodes and desaturation events by patient group.
Figure 7:
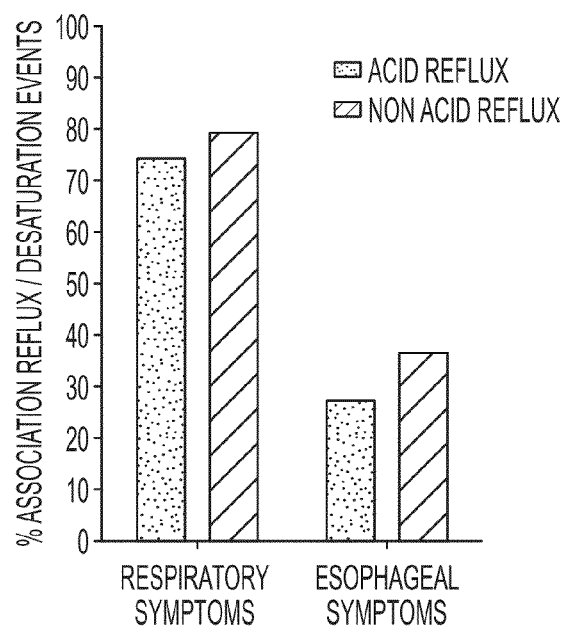
FIG. 7 is a bar chart of the association between acid and nonacid reflux episodes and desaturation events in patients with and without primary respiratory symptoms.

In patients with primary respiratory symptoms, 952 (85.2%) of the 1,117 reflux events were acid and 165 (14.8%) were nonacid. The mean number of reflux episodes in 24 h was 81±10 and the mean number of $O_2$ desaturations was 239±31. The mean $pO_2$ in 24 h detected by pulse oximetry was 93.9±0.5% (Table 2). Seventy-four percent (832/1,117) of the distal reflux events were associated with $O_2$ desaturation episodes (FIG. 5). This correlation was higher (80.3%, 453/564) for proximal reflux events (FIG. 6). Acid reflux was associated with desaturation episodes in 73.6% (701/952) of events, similar to the desaturation noted with nonacid reflux (79.4%, 131/165; FIG. 7). The average time from pH drop to <4 and $O_2$ desaturation was 127±7 s following a distal esophageal reflux event. This interval was significantly shorter following a proximal reflux event (85±19 s, p<0.005). The mean $pO_2$ drop during a desaturation episode was 9.0±0.2%.

TABLE 2

Reflux and $O_2$ Desaturation in Patients with Respiratory Symptoms and Those with Esophageal Symptoms

| | Respiratory symptoms (n = 20 patients) | Esophageal symptoms (n = 10 patients) | p value |
|---|---|---|---|
| Mean number of reflux episodes in 24 h | 81 (±10) | 80 (±16) | ns |
| Mean number of desaturations in 24 h | 239 (±31) | 119 (±34) | p < 0.005 |
| Time interval (s) from reflux to desaturation (mean) | 104 (±16) | 129 (±11) | p < 0.05 |
| Time interval (s) from proximal reflux to desaturation | 85 (±19) | 121 (±14) | p < 0.005 * p < 0.05 |
| Time interval (s) from distal reflux to desaturation | 127 (±7) | 139 (±17) | ns |
| $pO_2$ drop of a desaturation episode (mean) | 9% (±0.2) | 9% (±0.2) | ns |
| $pO_2$ peak of a desaturation correlated with reflux event (mean) | 87.2% (±0.16) | 87.8% (±0.25) | ns |
| Mean $pO_2$ in 24 ha | 93.92% (±0.48) | 95.36% (±0.4) | p < 0.05 |

Figure 8:
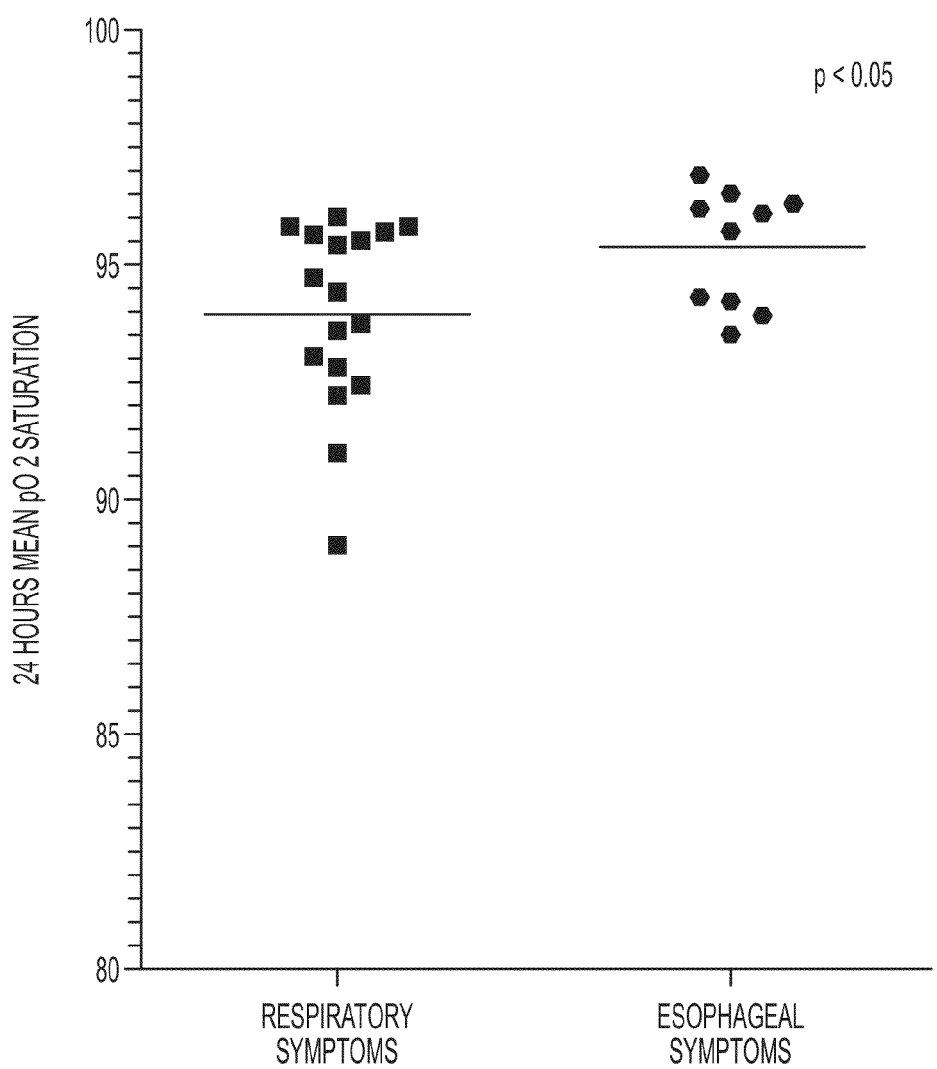
FIG. 8 is a scatter plot of 24-h mean oxygen saturation in 18 patients with primary respiratory symptoms that had completed 24-h continuous monitoring by MII-pH and pulse oximetry and in ten patients with primary esophageal symptoms.

Ten patients had primary esophageal reflux symptoms. MII-pH monitoring detected a total of 734 reflux episodes in these patients, of which 589 (80.2%) were acid and 145 (19.8%) were nonacid. The mean number of reflux episodes per 24 h (80±16) was similar to the respiratory group, while the mean number of $O_2$ desaturation events was significantly less (119±34). The mean $pO_2$ in 24 h detected by pulse oximetry was 95.4±0.4% (FIG. 8). Acid reflux was associated with desaturation episodes in 29% of events (170/589), and non-acid reflux was associated with desaturation in 36.6% (53/145), both significantly less than in patients with primary respiratory symptoms. The reflux-desaturation association was even more marked when proximal reflux events were compared: 80.3% (453/564) of reflux events were associated with desaturation in patients with respiratory symptoms and 29.4% (126/428) in patients with esophageal symptoms (p<0.0001). The mean drop in oxygen saturation associated with reflux episodes was similar in the two groups (9.0±0.2%; Table 2).

Our data show a remarkably high prevalence of oxygen desaturation events associated with gastroesophageal reflux in patients with respiratory symptoms. These reflux-associated desaturations are much more prevalent in patients with primary respiratory symptoms than in those with primary typical symptoms. While our data do not prove that reflux is causing the desaturation events, the temporal correlation is intriguing and suggests that reflux may be etiologic.

Further experimental data from subsequent studies will now be presented.

Figure 9:
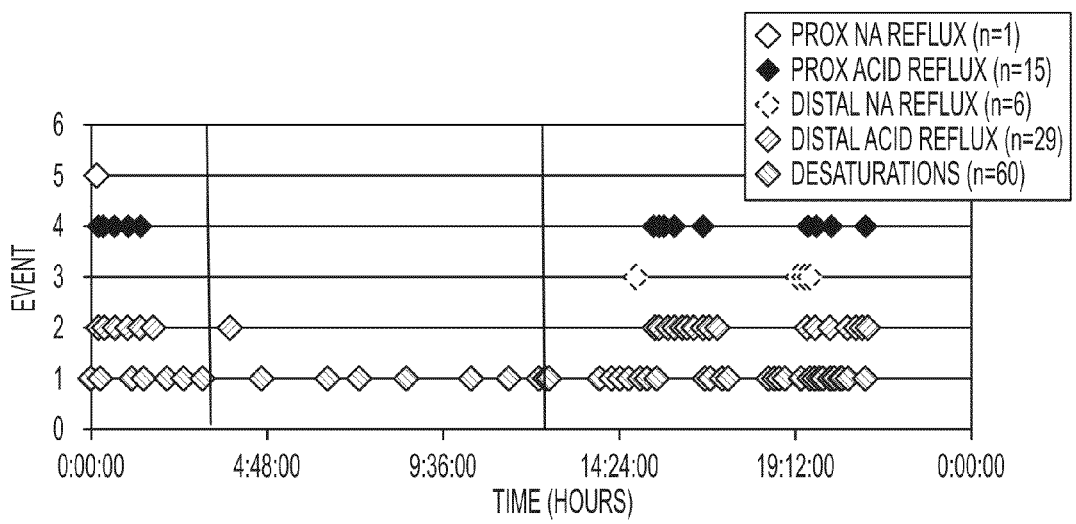
FIG. 9 is a scatter plot depicting the temporal relationship between reflux episodes and oxygen desaturation events over a 24 hour time period for one subject.

Subjects/patients underwent simultaneous dual-channel esophageal impedance-pH testing and ambulatory pulse-oximetry monitoring continuously for a period of 24 hours. Reflux episodes were defined as the detection of refluxate with a pH<4 5 cm above LES (20 cm above the LES defined as proximal reflux), and/or a drop ≥50% from baseline in impedance recordings 3, 5, 7, 9 cm above LES (15 and 17 cm above LES defined as proximal reflux). Oxygen desaturation events were defined by either a drop in the oxygen saturation to <90%, or a drop by a margin of ≥6% from baseline. Associations between reflux episodes and oxygen desaturation events were determined by correlating the temporal relationship of these events over the 24 hour period. A Reflux-Associated Desaturation (RAD) was then defined as the first oxygen desaturation event occurring within the 10 minute interval following a reflux episode, and the time taken to desaturate from the start of the reflux episode for each association was calculated. Total and proximal RAD episodes are expressed as a percentage of the total and proximal number of reflux episodes, respectively. FIG. 9 shows a scatter plot depicting the temporal relationship between reflux episodes and oxygen desaturation events over a 24 hour time period for one subject.

Figure 10:
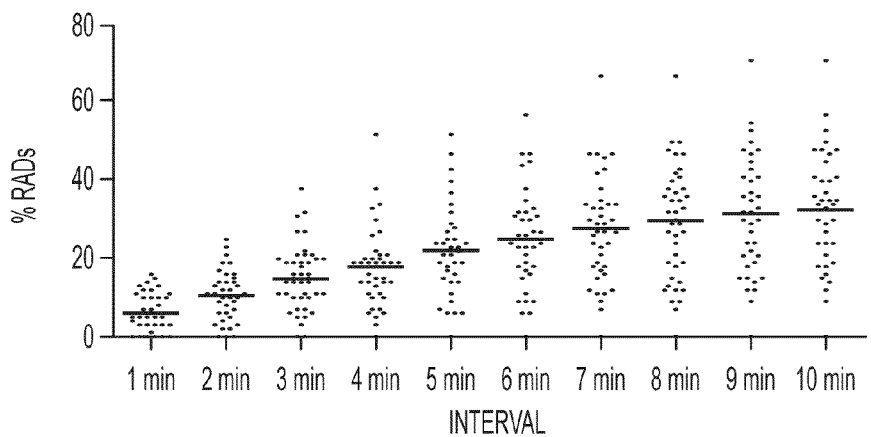
FIG. 10 is a scatter plot of % total RAD episodes per subject for 10 consecutive 1 minute intervals, respectively, indicating plateau of RAD at approximately 30-35% starting from the 6th minute interval.

The Frequency of Reflux Associated Oxygen Desaturations; Establishment of Normative Data:

In 36 subjects, a total of 1293 reflux episodes were detected on dual channel impedance-pH monitoring, of which 64% (825/1293) were acid and 36% (470/1293) non-acid. 39% (501/1293) of the total episodes extended proximally, with 69% (344/501) acid and 31% (157/501) non-acid reflux. Within the 24 hour period a total of 3106 oxygen desaturation events occurred, median of 72 (28-183), with the majority occurring in the upright position. 32% (410/1293) of the total reflux events were associated with oxygen desaturation events, 30% (251/825) of the total acid episodes and 34% (159/470) of the total non-acid episodes. Associations were also apparent in 38% (188/501) of the proximal impedance-pH events, 38% (130/344) of the proximal acid and 40% (58/157) of the proximal non-acid events. FIG. 10 shows a scatter plot of % total RAD episodes per subject for 10 consecutive 1 minute intervals, respectively; indicating plateau of RAD at approximately 30-35% starting from the $6^{th}$ minute interval.

The Frequency of Reflux Associated Oxygen Desaturations:

A previous study (Salvador et al. Association of Gastroesophageal Reflux and O2 Desaturation: A Novel Study of Simultaneous 24-h MII-pH and Continuous Pulse Oximetry. J Gastrointest Surg 2009, 13:854-861), based on similar methodology, showed a 60% association between reflux episodes and oxygen desaturation events in symptomatic patients with both typical (n=10) and atypical (n=20) complaints. This study revealed that more associations were evident in the group of patients with primary respiratory symptoms (75%, 832/1117) than in those with primary gastrointestinal symptoms (30%, 223/734, p<0.0001).

TABLE 3

Comparison of RAD episodes occurring in normal subjects versus the two groups of symptomatic patients described in the study above.

|  | Normals (n = 36) | Resp Group (n = 20) | GI Group (n = 10) |
| --- | --- | --- | --- |
| Total desaturation episodes | 3106 | — | — |
| Mean desaturation episodes (SD) | 86 (±42) | 239 (±31) | 119 (±34) |
| Total RAD episodes in 10 mins | 32% (410/1293) | 74% (832/1117) | 30% (223/734) |
| Mean RAD episodes in 10 mins (SD) | 11 (±7) | — | — |
| Acid RAD episodes in 10 mins | 30% (251/825) | 74% (701/952) | 29% (170/589) |
| Mean acid RAD episodes in 10 mins (SD) | 7 (±5) | — | — |
| Non-acid RAD episodes in 10 mins | 34% (159/470) | 79% (131/165) | 37% (53/145) |
| Mean non-acid RAD episodes in 10 mins (SD) | 4 (±4) | — | — |
| Time to desaturation (seconds) | — | 127 (±7) | 139 (±17) |
| Mean time to desat (SD) | 254 (±71) | 104 (±16) | 129 (±11) |

CONCLUSIONS

A higher prevalence of oxygen desaturations associated with gastroesophageal reflux in patients presenting with primary respiratory symptoms is evident. This relationship is further validated by findings in normal subjects that approximate those in patients with typical reflux complaints.

A further 32 patients, 24 with primary respiratory and 8 with primary gastrointestinal symptoms, have been recruited and have undergone the 24-hour impedance-pH and pulse-oximetry monitoring. The results for this subgroup of patients will be electronically analysed on completion of the development and implementation of an automated software programme (discussed below) specifically designed to facilitate the timely analysis of these data sets and to eliminate the element of human error from the manual analysis.

Figure 11:
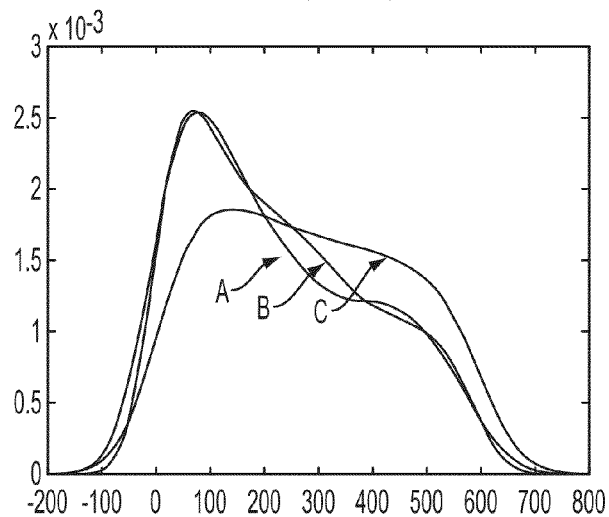
FIG. 11 is a graph depicting shorter time taken to desaturation from reflux for patients with respiratory symptoms and patients with gastrointestinal symptoms, than for normal subjects.

Further validation of the correlation between reflux and oxygen desaturation episodes is evident from the finding that a shorter time to desaturation is noted in both groups of these 32 symptomatic patients when compared to the group of normal subjects. A possible explanation for this being hypersensitisation of the vagally-mediated esophagobronchial reflex as a result of repetitive exposure of the nerve-endings in the distal esophagus to refluxate from gastroesophageal reflux, causing mucosal injury. The overall effect results in decreased airway flow and a shorter time to oxygen desaturation. FIG. 11 is a graph depicting shorter time taken to desaturation from reflux for patients with respiratory symptoms (curve A) and patients with gastrointestinal symptoms (curve B), than for normal subjects (curve C).

The Effect of Nissen Fundoplication on Reflux Associated Desaturations:

Although in the early phase, symptomatic patients are also being recruited to undergo determination of the frequency of RADs pre- and post-Nissen fundoplication. The rationale for this study is to ascertain whether the surgical correction of gastroesophageal reflux by Nissen fundoplication has any reducing effect on the prevalence of RADs following surgical intervention. 40 subjects is the target; however, only 4 are enrolled, and only one has undergone complete testing.

Identification of Artifacts

Figure 12A:
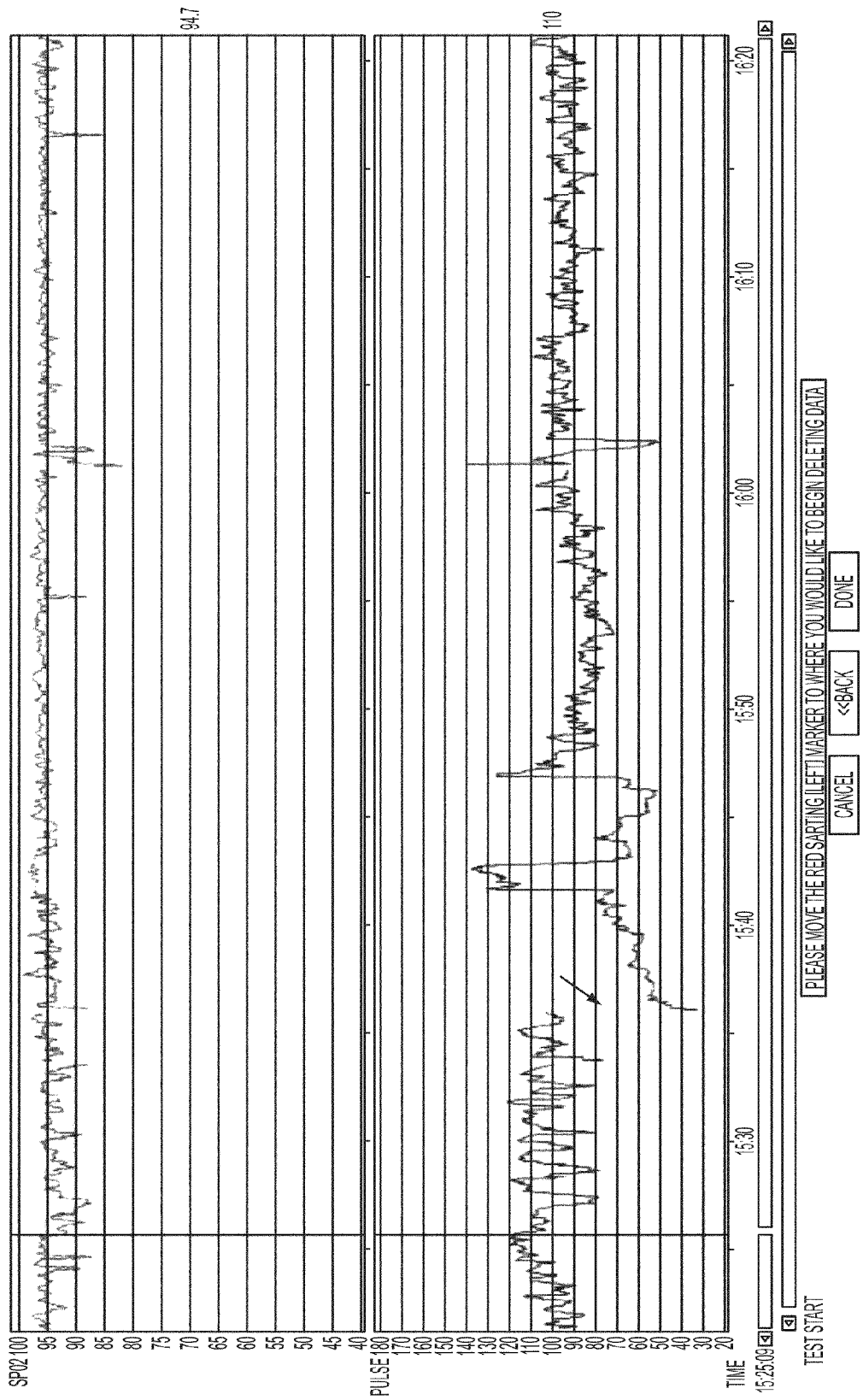
FIGS. 12A-12G are graphs showing patterns of artifacts.
Figure 12B:
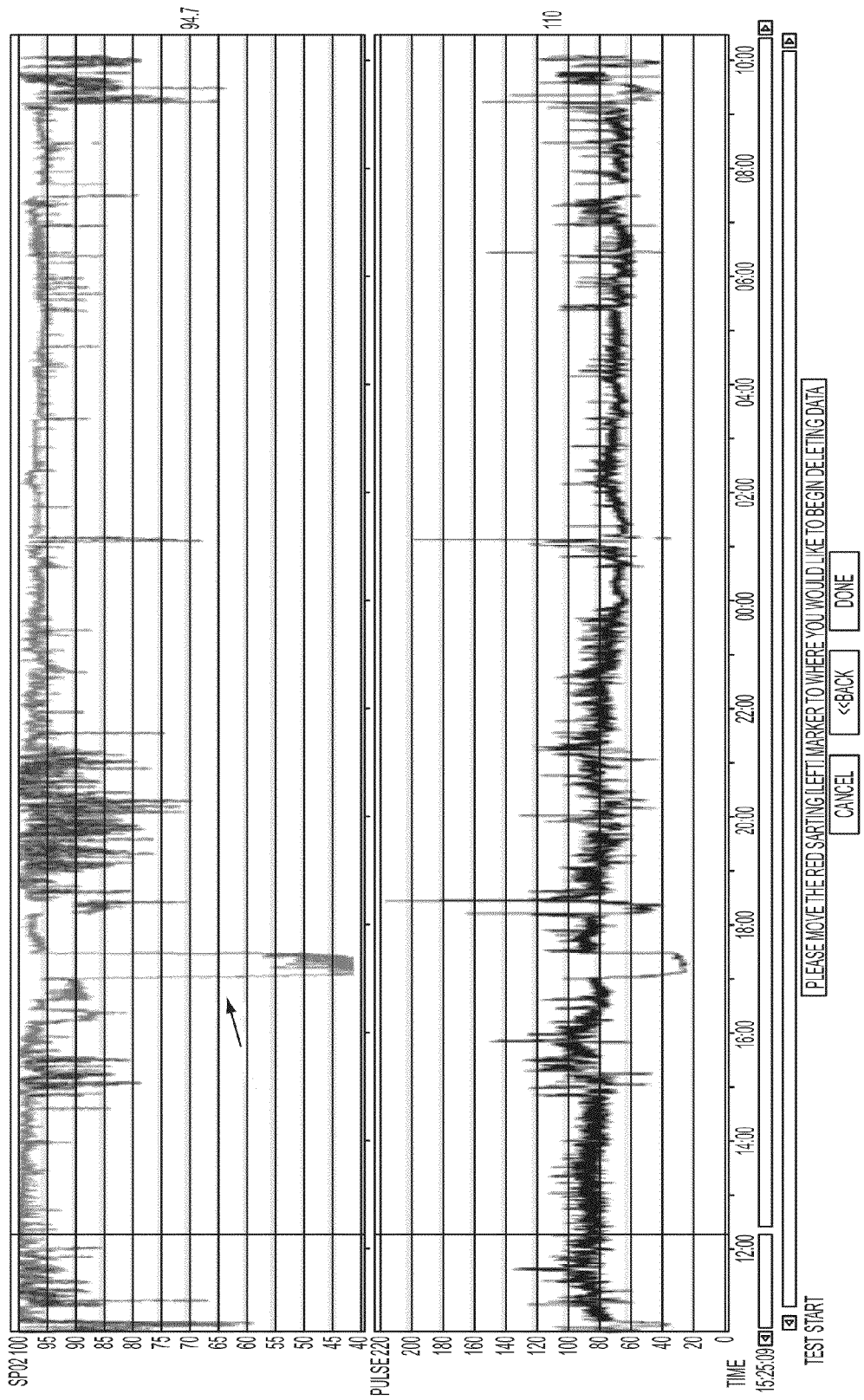
Figure 12C:
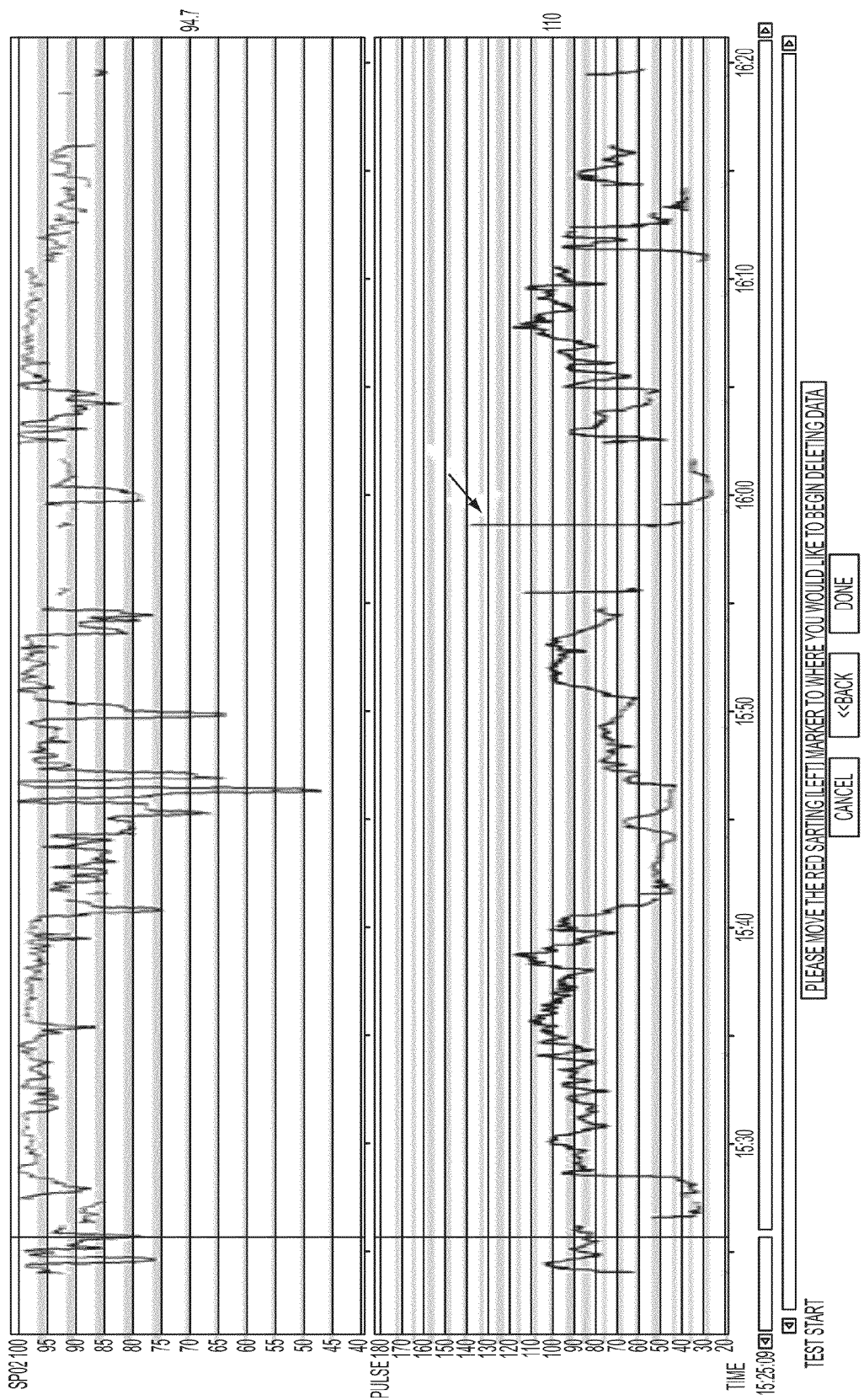
Figure 12D:
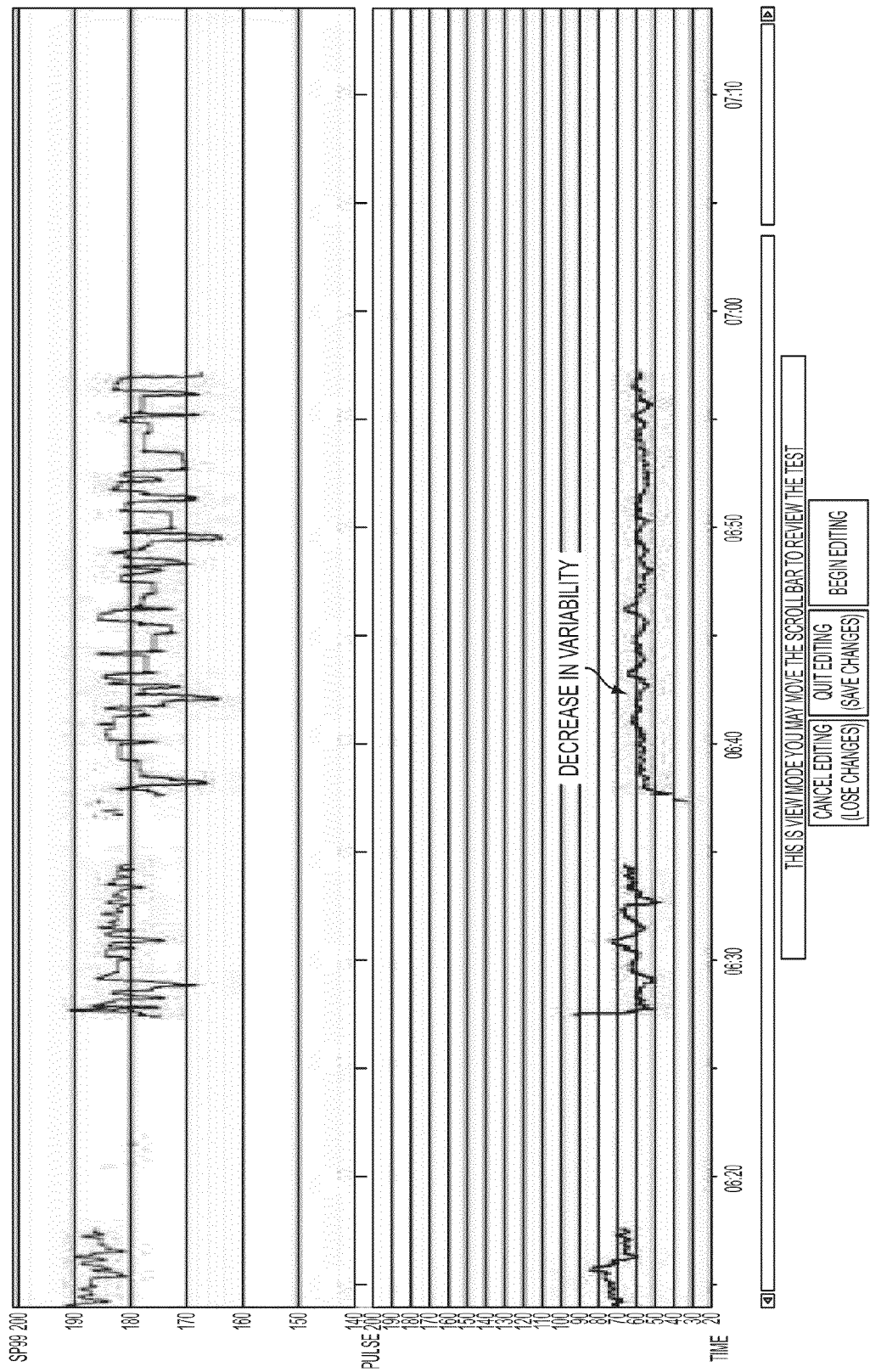
Figure 12E:
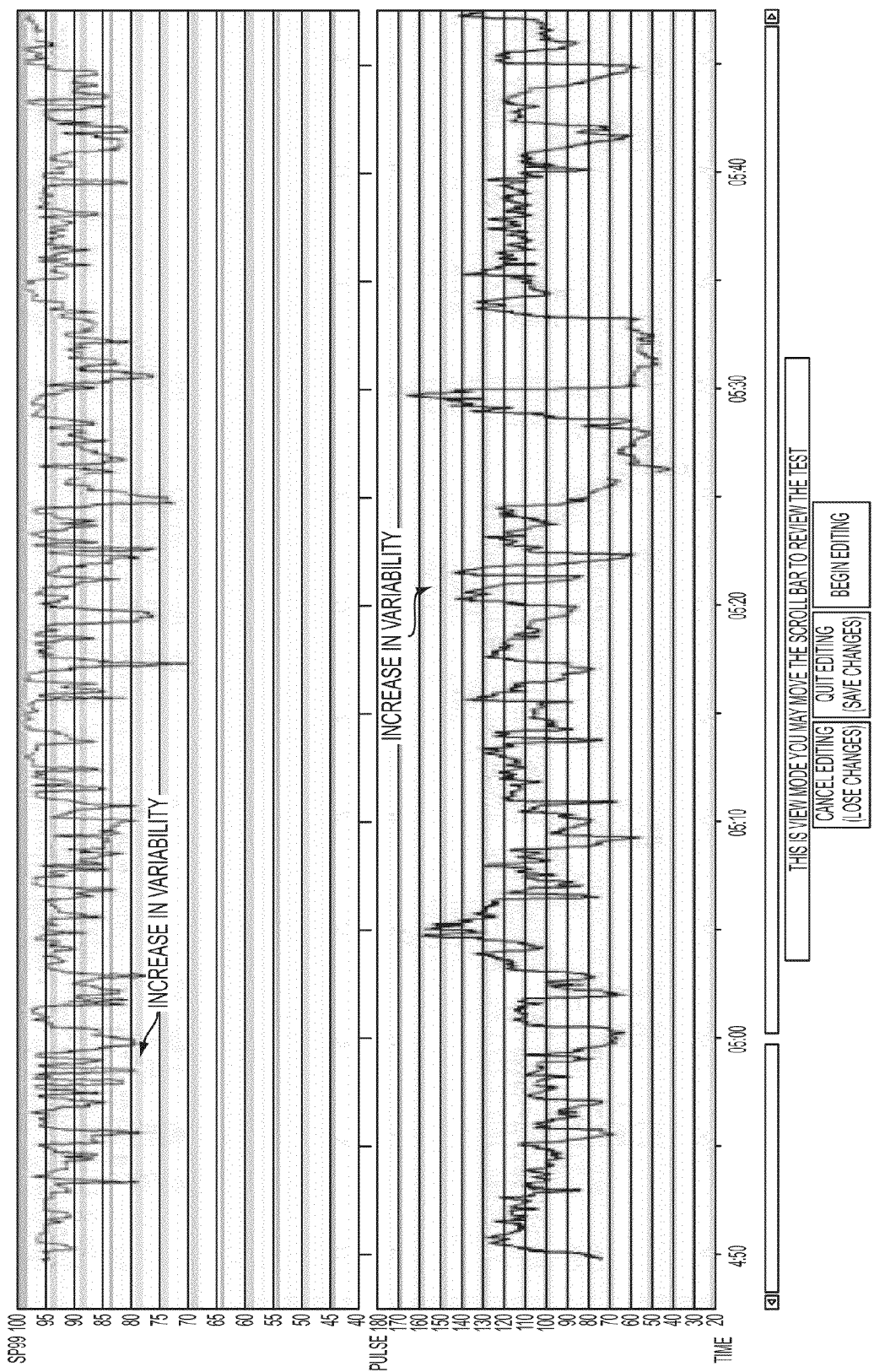
Figure 12F:
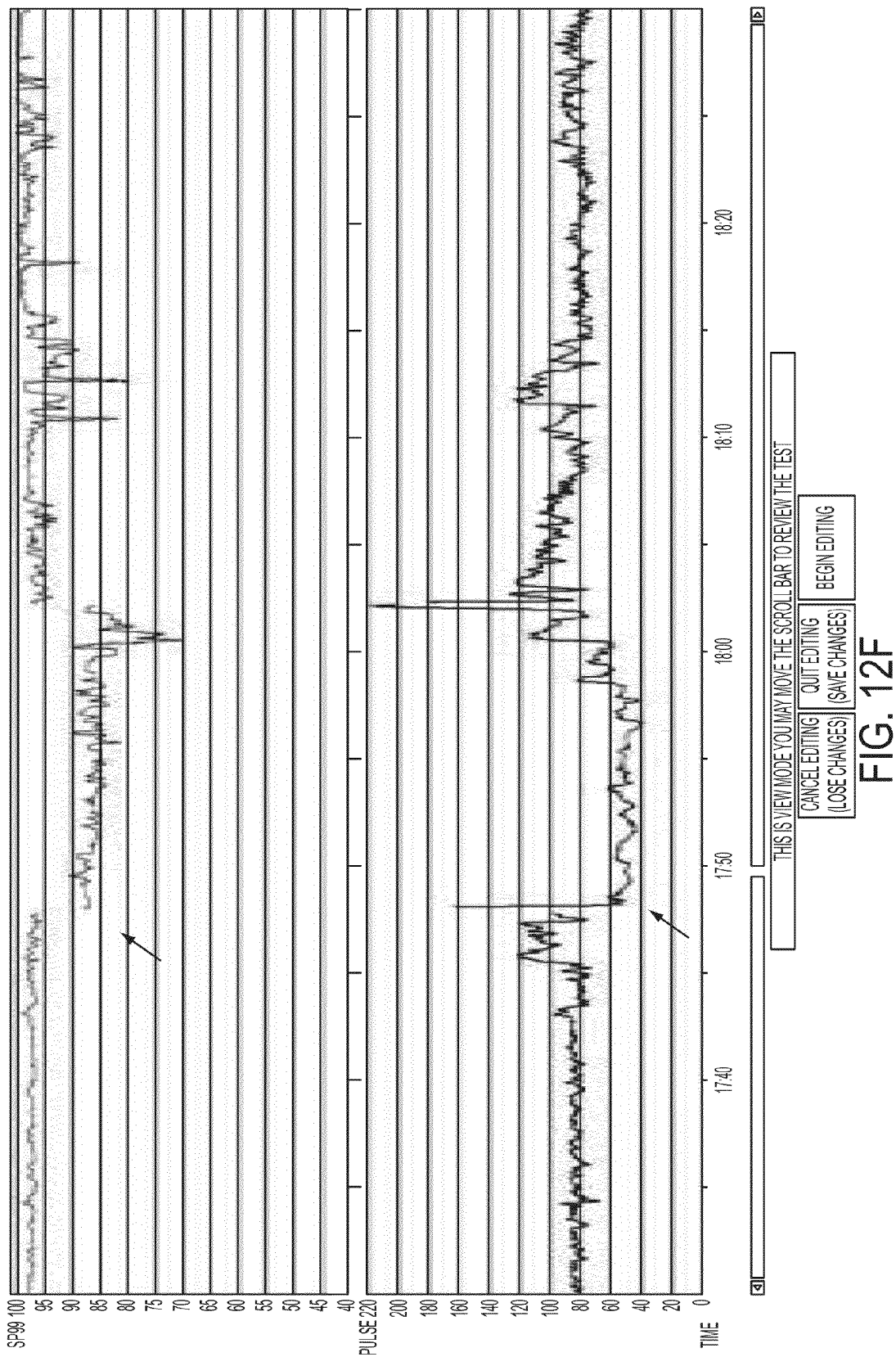
Figure 12G:
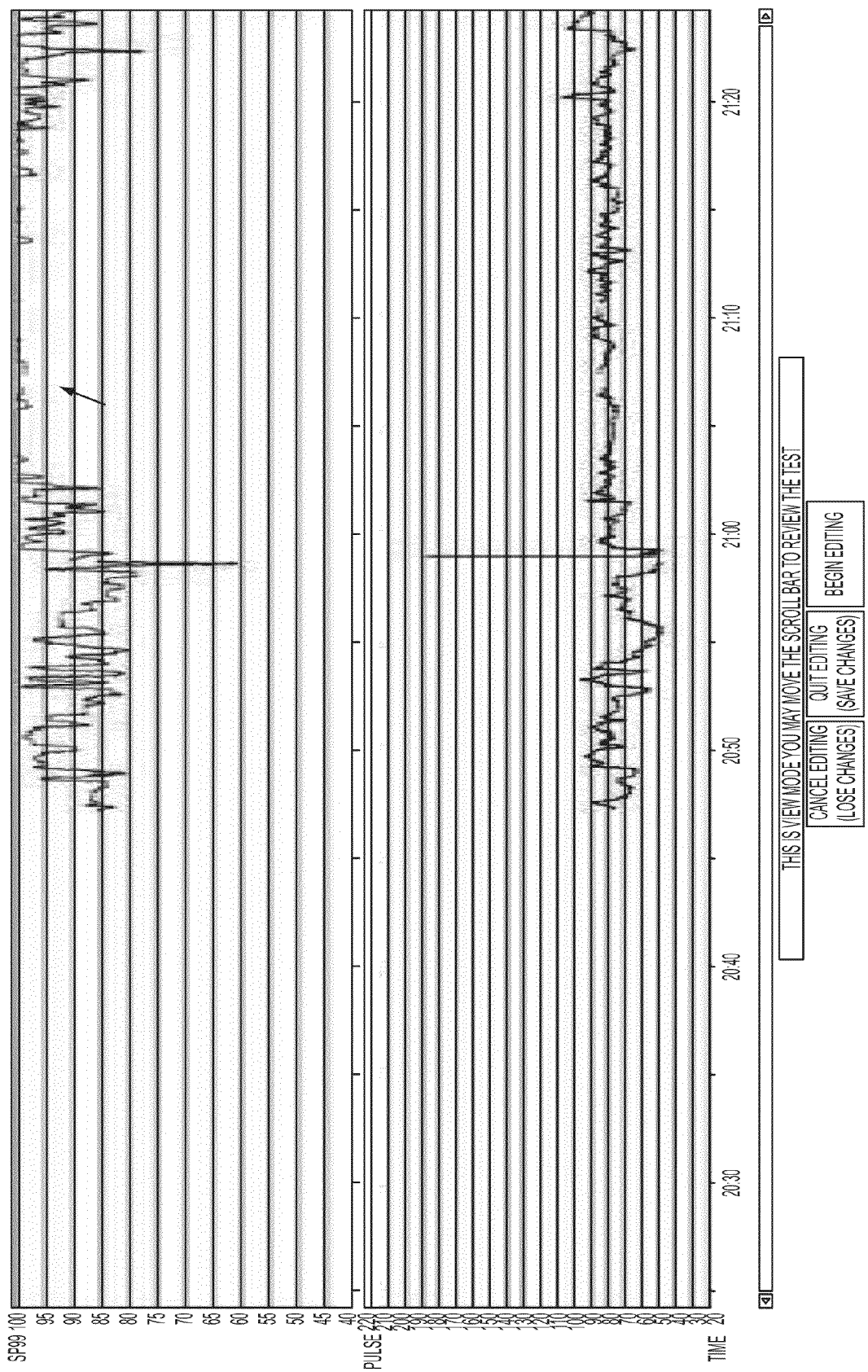

Due to the prolonged ambulatory monitoring period, both recordings are prone to a variety of artifacts. This is particularly relevant to the pulse-oximetry monitoring, as the finger-probe sensor is subject to significant motion/disruption, predominantly as a result of its location. These technical artifacts are commonly falsely interpreted as desaturations by the recording software and inclusion of this aberrant data may skew results, yielding a falsely elevated number of correlations with reflux events. Therefore, a manual hand analysis is required for each tracing to evaluate and differentiate these false positive readings from the true positive desaturations. Automation of this analysis is in the process of development as accurate definition are currently being established. 6 patterns of artifacts have been identified to date and are required to be excluded prior to identifying correlations:

1. Break in data recording (loss of contact between sensor and signal) (FIG. 12A)
2. Rate of desaturation/resaturation >4%/s (too rapid to be physiological) (FIG. 12B)
3. Aberrant points (unlikely physiological) (FIG. 12C):
   3a. single points of saturation ≥10 from prior and subsequent points
   3b. single points of pulse ≥20 from prior and subsequent points
4. Changes in variability of waveform amplitude (poor signal, motion) (FIGS. 12D and 12E)
5. Baseline shifts for ≥3 minutes (malpositioning of sensor relative to signal) (FIG. 12F)
6. Locked value/plateau for ≥8 seconds (decreased pulsatility of signal) (FIG. 12G)

Figure 13:
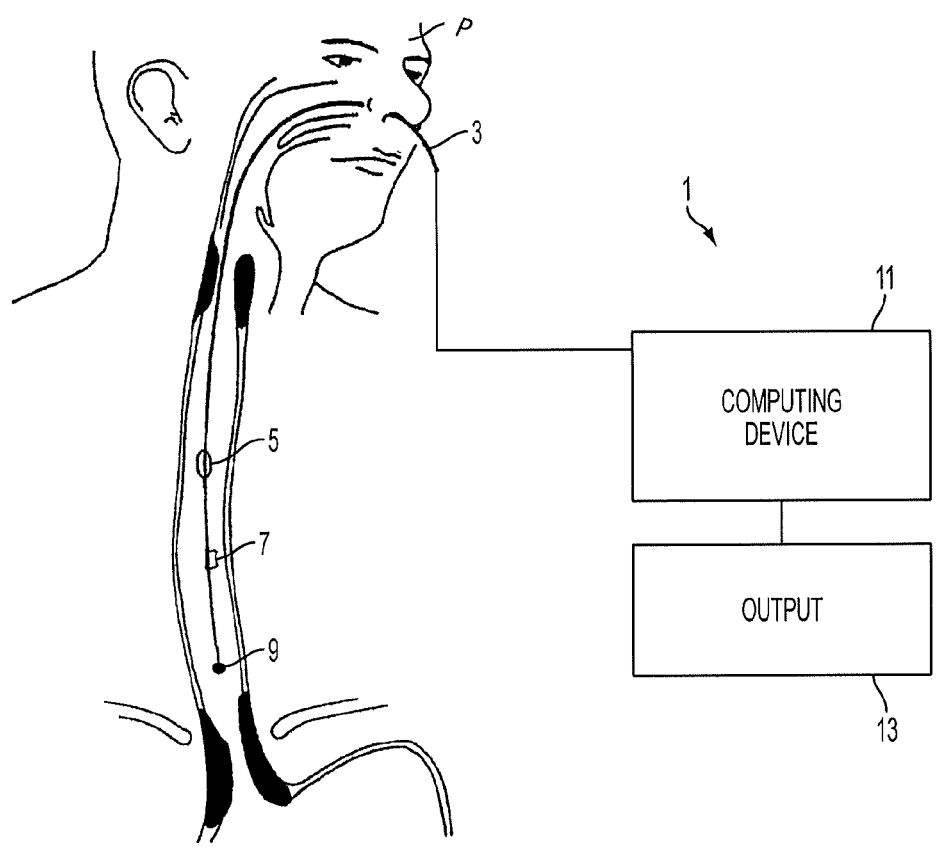
FIG. 13 is a schematic diagram of a diagnostic instrument according to the preferred embodiment.

A device for diagnosis will now be disclosed with reference to FIG. 13. The device 1 includes a 1-2 mm plastic catheter 3 for use in a patient P, with sensors 5, 7, 9 comprising one or more antimony type pH sensors, multiple impedance sensors and one or more oxygen saturation sensors. Also possible is an implantable device with a single pH and $O_2$ sensor. Similar devices currently exist with antimony based pH sensors, but to the inventors' knowledge not the combination of $O_2$ saturation and pH. A computing device 11 receives signals from the sensors, processes them, and provides an output on an output device 13, which can include one or more of a printer, a display, persistent storage, and a communication link to a remote location.

The device can be designed to simultaneously measure pH and oxygen saturation at one or more sites in the upper aerodigestive tract. It can be implanted in the pharynx, esophagus and/or stomach for a suitable time period such as 24-48 hours. It can be implanted through transnasal placement of a small caliber catheter position based upon endoscopic or manometric measures or temporary implantation onto the mucosa of the esophagus or stomach.

A diagnostic algorithm can be implemented along the following lines. Reflux is defined by the occurrence of pH<4 or reflux in the two proximal impedance sensors. An abnormal 24-hour MII-pH study is defined as a DeMeester score >14.72 or the presence of more than 26 weakly acidic reflux episodes or one alkaline reflux episode (pH>7). Oxygen desaturation events were defined by one of two observations: 1) $SpO_2$<90%; or 2) $SpO_2$ drop of 6% or greater. A reflux-desaturation association was considered present if $O_2$ desaturation occurred within 30 seconds prior to or 10 minutes after a reflux event.

The Pulse Oxidation Desaturation Event Scoring System (PODESS) is a clinical software development project with the final objective of assigning an assessment score to a patient quantifying the correlation between the patient's respiratory symptoms and underlying gastroesophageal reflux disease. This will facilitate the appropriate decision-making process for subsequent treatment options to determine whether such patients would benefit from surgical versus non-surgical management. In order to achieve this objective, there will be multiple phases of the project that will adhere to the standard software development lifecycle process. The software will have components of functionality reflecting the following capabilities: data import processes for patient results from both the impedance-pH and pulse-oximetry systems as well as the ability to export data that is generated during the analysis phase to enhance answering ad-hoc analytical questions. The system will be able to automatically generate the identification of pre-determined events such as RAD events and episodes of data artifact; these critical in supporting the simulation component of the software. The simulation portion of the software will facilitate the efficient processing of large quantitative data, provide great flexibility through the end user's ability to change the level of parameters, and allow for algorithmic testing. The final phase of the project will be to embed all previous functionality into a web based tool for the utilization by physicians and surgeons globally. The successful completion of this project will represent a major advance in attaining diagnostic sensitivity and specificity in this group of patients and aid as a guide to their appropriate management.

While a preferred embodiment has been set forth above, those skilled in the art who have reviewed the present disclosure will readily appreciate that other embodiments can be realized within the scope of the present invention. For example, numerical values are illustrative rather than limiting, as are recitations of specific types of sensors. Therefore, the present invention should be construed as limited only by the appended claims.

What is claimed is:

1. A method for diagnosing respiratory diseases related to gastroesophageal reflux disease in a patient, the method comprising:
 (a) providing a catheter having sensors for detecting esophageal or pharyngeal impedance, pH, and oxygen saturation in the patient;
 (b) inserting the catheter into an esophagus or pharynx of the patient;
 (c) detecting the esophageal or pharyngeal impedance and the pH in the patient, using the sensors;
 (d) detecting the oxygen saturation in the patient, using the sensors;
 (e) importing the esophageal or pharyngeal impedance and the pH detected in step (c) and the oxygen saturation detected in step (d) into a computing device; and
 (f) processing the esophageal or pharyngeal impedance and the pH detected in step (c) and the oxygen saturation detected in step (d) in the computing device to determine a time of a reflux event and a time of an oxygen desaturation event, to determine a reflux-desaturation association if the oxygen desaturation event occurs within a given time period of the reflux event, and to diagnose the respiratory diseases from the reflux-desaturation association.

2. The method of claim 1, wherein the sensors comprise a plurality of impedance sensors, and wherein step (c) comprises detecting the impedance using the plurality of impedance sensors.

3. The method of claim 2, wherein step (f) comprises determining that the patient is experiencing the reflux event if either the pH is below a threshold or the reflux event is detected in two of the plurality of impedance sensors.

4. The method of claim 1, wherein step (f) comprises detecting an abnormal multichannel intraluminal impedance-pH study if step (f) results in a determination that:
 (i) a DeMeester score exceeds a threshold;
 (ii) a number of acidic reflux episodes exceeding a predetermined number are detected; or
 (iii) an alkaline reflux episode is detected.

5. The method of claim 1, wherein step (f) comprises:
 (i) determining $SpO_2$; and
 (ii) detecting the oxygen desaturation event if either (A) the $SpO_2$ is below a first threshold or (B) the $SpO_2$ drops by more than a second threshold.

6. The method of claim 1, wherein:
 the sensors comprise at least one pH sensor, a plurality of impedance sensors, and at least one oxygen sensor;
 step (c) is performed using the at least one pH sensor and the plurality of impedance sensors; and
 step (d) is performed using the at least one oxygen sensor.

7. The method of claim 6, wherein the at least one pH sensor is an antimony type pH sensor.

8. A system for diagnosing respiratory diseases related to gastroesophageal reflux disease in a patient, the system comprising:
 a catheter configured to be insertable into an esophagus or pharynx of the patient;
 a sensor, disposed on the catheter, for detecting esophageal or pharyngeal impedance in the patient;
 a sensor, disposed on the catheter, for detecting pH in the patient;
 a sensor, disposed on the catheter, for detecting oxygen saturation in the patient; and
 a computing device, in communication with the sensors, configured for processing the esophageal or pharyngeal impedance, the pH and the oxygen saturation to determine a time of a reflux event and a time of an oxygen desaturation event, to determine a reflux-desaturation association if the oxygen desaturation event occurs within a given time period of the reflux event, and to diagnose the respiratory diseases from the reflux-desaturation association.

9. The system of claim 8, wherein the sensor for detecting esophageal or pharyngeal impedance in the patient comprises a plurality of impedance sensors, and wherein the computing device is configured for detecting the impedance using the plurality of impedance sensors.

10. The system of claim 9, wherein the computing device is configured for determining that the patient is experiencing the reflux event if either the pH is below a threshold or the reflux event is detected in two of the plurality of impedance sensors.

11. The system of claim 8, wherein the computing device is configured for detecting an abnormal multichannel intraluminal impedance-pH study if the processing performed by the computing device results in a determination that:
 (i) a DeMeester score exceeds a threshold;
 (ii) a number of acidic reflux episodes exceeding a predetermined number are detected; or
 (iii) an alkaline reflux episode is detected.

12. The system of claim 8, wherein the computing device is configured for:
(i) determining $SpO_2$; and
(ii) detecting the oxygen desaturation event if either (A) the $SpO_2$ is below a first threshold or (B) the $SpO_2$ drops by more than a second threshold.

13. The system of claim 8, wherein the sensors comprise:
at least one pH sensor;
a plurality of impedance sensors; and
at least one oxygen sensor.

14. The system of claim 13, wherein the at least one pH sensor is an antimony type pH sensor.

* * * * *